United States Patent [19]

Greene

[11] 4,301,087

[45] Nov. 17, 1981

[54] MANUFACTURE OF CARBAMATES FROM CYANOGEN

[75] Inventor: Janice L. Greene, Chagrin Falls, Ohio

[73] Assignee: Standard Oil Company, Cleveland, Ohio

[21] Appl. No.: 179,148

[22] Filed: Aug. 18, 1980

[51] Int. Cl.³ .................. C07C 125/04; C07C 119/18; C07C 119/20; C07C 68/00

[52] U.S. Cl. .................. 260/463; 260/453.7; 560/132; 560/133; 560/134; 560/157; 560/162; 560/166

[58] Field of Search ............... 560/157, 132, 133, 134, 560/162, 166; 260/453 R, 453.7, 463

[56] References Cited

U.S. PATENT DOCUMENTS

| | | | |
|---|---|---|---|
| 2,819,292 | 1/1958 | Welcher | 560/157 |
| 3,170,947 | 2/1965 | Gruber | 260/453.7 |
| 3,301,883 | 1/1967 | Gruber | 260/453.7 |

FOREIGN PATENT DOCUMENTS

| | | | |
|---|---|---|---|
| 1468526 | 12/1968 | Fed. Rep. of Germany | 260/453 R |
| 2426913 | 12/1975 | Fed. Rep. of Germany | 260/453 R |

OTHER PUBLICATIONS

Fahnenstich, Chemiker-Zertung, 96 pp. 388-396 (1972).

*Primary Examiner*—Natalie Trousof
*Assistant Examiner*—Michael Shippen
*Attorney, Agent, or Firm*—Gary R. Plotecher; Herbert D. Knudsen; Larry W. Evans

[57] ABSTRACT

Carbamates, such as ethyl carbamate, are prepared by contacting an alcohol, such as ethanol, with cyanogen and water in the presence of a dipolar, aprotic solvent, such as acetonitrile, and an acid catalyst, such as hydrochloric acid.

11 Claims, No Drawings

MANUFACTURE OF CARBAMATES FROM CYANOGEN

BACKGROUND OF THE INVENTION

1. Field of the Invention

This invention relates to the conversion of cyanogen. In one aspect the invention relates to the conversion of cyanogen with an alcohol and water to a carbamate while in another aspect, the invention relates to the concomitant manufacture of dialiphatic, dialicyclic or diaryl imidocarbonates.

2. Description of the Prior Art

Cyanogen (NC—CN) is a well known, industrial compound. It is easily prepared by any one of a number of well known methods of which slowly dropping a solution of potassium cyanide into a solution of copper sulfate and heating mercury cyanide are just two. Industrial uses include a heat source for welding and cutting metals, a fumigant, a rocket propellant and general organic synthesis. On the latter, Fahneustich, et al., *Chemiker-Zeitung*, 96, pp. 388–395 (1972), detail a number of reactions in which cyanogen is converted to some other useful product. However to date cyanogen has not been used to prepare carbamates or dialiphatic, dialicyclic or diaryl imidocarbonates.

SUMMARY OF THE INVENTION

According to this invention, carbamates of the formula:

$$R-O-\overset{O}{\underset{\|}{C}}-NH_2 \quad (I)$$

are prepared by a process comprising contacting an alcohol of the formula:

$$R-(OH)_n \quad (II)$$

with cyanogen and water in the presence of dipolar, aprotic solvent and an acid catalyst, where R is an aliphatic, alicyclic or aryl radical and n is a positive integer, typically 1–6. In many instances, this process concomitantly produces dialiphatic, dialicyclic or diaryl imidocarbonates.

DETAILED DESCRIPTION OF THE INVENTION

As indicated earlier, cyanogen is a well known, commercially available compound. At room temperature it is a colorless gas having a pungent, penetrating odor. Both technical and pure grade cyanogen can be used in this invention. If desired, the cyanogen can be mixed with a diluent but this is generally not preferred.

The alcohols here used (formula II) include both aliphatic and aryl alcohols. The aliphatic and alicyclic alcohols typically contain 1 and about 30 carbon atoms and preferably between about 1 and 10 carbon atoms. Primary, secondary and tertiary aliphatic and alicyclic alcohols can be used as well as both saturated and unsaturated. The aryl alcohols include those of one benzene nuclei (phenyl radical), two or more fused benzene nuclei (e.g. naphthyl radical) and two or more non-fused benzene nuclei (e.g. biphenyl radical). The alcohols of this invention contain at least one hydroxyl group (—OH) but can contain two or more hydroxyl radicals per molecule. Representative alcohols include methanol, ethanol, neopentyl alcohol, diethylene glycol, cyclohexanol, phenol, alpha-naphthol, resorcinol, various saccharides, etc. The saturated, primary aliphatic alcohols, such as methanol and ethanol are preferred. Tertiary aliphatic alcohols, e.g. t-butanol are least preferred. Although the alcohols of this invention can be used either alone or in combination with one another, they are preferably used alone. Moreover, these alcohols can bear one or more inert substituents, i.e. substituents that are essentially nonreactive with the starting materials, catalysts and products of a process at process conditions, but preferably the alcohols are free of such substituents. Representative substituents include alkyl, aryl, halide and alkoxy radicals.

The solvents of this invention are dipolar, aprotic materials. These solvents are essentially nonreactive with the starting materials, catalysts and products of the process at process conditions. Aliphatic, alicyclic and aromatic nitriles, ethers, sulfones and phosphoamides are representative of the classes of solvents here used with specific examples including acetonitrile, propionitrile, butyronitrile, adiponitrile, benzonitrile, toluinitrile, tetrahydrofuran, dioxane, dimethoxymethane, glyme, diglyme, anisole, tetramethylene sulfone, dipropyl sulfone, hexamethyl phosphoamide, etc. Sufficient solvent to solublize both the cyanogen and alcohol is used.

Any acid catalyst of sufficient strength to protonate cyanogen or to generate a material from the reaction mass that can protonate cyanogen can be used in the practice of this invention. These catalysts can be gaseous, liquid or solid and include such diverse materials as boron trifluoride, sulfur dioxide, sulfur trioxide, hydrogen fluoride, sulfuric acid, phosphoric acid, hydrogen bromide, hydrochloric acid, hydrogen iodide, aluminum phosphate, zirconium phosphate, calcium nickel phosphate, phosphotungstic acid, phosphomolybdic acid and the like. Other acids include the various acid forms of zeolites and ion exchange resins. The hydrohalic, e.g. hydrochloric, hydrobromic, etc., acids are preferred.

Sufficient catalyst is used to catalyze the reaction between alcohol, water and cyanogen. This amount is a catalytic amount and typically is at least about 0.0001 mole per mole of cyanogen, and preferably about 0.01 mole. Economy and convenience are the only constraints upon the maximum amount of acid that can be employed with a typical maximum being about 1 mole per mole of cyanogen and preferably about 0.1 mole.

The reaction is typically conducted in the liquid state, the cyanogen, alcohol, water and catalyst either dissolved or suspended in the aprotic solvent. Sufficient mixing of the reactants is usually provided to allow good contacts between these materials.

The water necessary to this invention can be added in any manner. For example the water can be added as free water or it can be added as part of one of the other reagents, e.g. the alcohol or catalyst. A stoichiometric amount of water is required but an excess (over cyanogen) is preferred to promote complete consumption of the cyanogen.

The temperature at which this process can be conducted can vary widely. Typically the temperature ranges from about 15° C. to about 250° C. with a preferred range of about 25° C. to about 150° C. Pressure can also vary widely and is important only in its relationship to the reaction temperature. Consequently, any pressure from subatmospheric to superatmospheric can be employed with autogeneous pressure preferred.

Stoichiometric amounts of alcohol and cyanogen are required for the practice of this invention but preferably the alcohol is present in an excess. Such an excess favors a quantitative conversion of the cyanogen.

The products of this invention are carbamates (formula I). These materials are useful intermediates in the manufacture of a wide variety of compounds, including pesticides, polyamides, polyurethanes and polycarbonates.

Other products concomitantly made by this process are dialiphatic, dialicyclic or diaryl imidocarbonates of the formula:

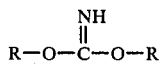
(III)

where R has the same definition as in formulae I and II. Obviously, when the starting material is a mixture of alcohols, each R of formula III can be the same or different. These products are useful intermediates in the production of various products, including polycarbonates, etc.

Yet another product that can be made by this invention is an ester of isocyanic acid. For instance, ethanol and cyanogen react in the presence of an acid catalyst and a dipolar, aprotic solvent to form ethyl cyanate which can then rearrange to form ethyl isocyanate.

While not being bound to theory, the alcohol and cyanogen are believed to react to form a compound of the formula

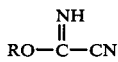
(IV)

Compound IV is then decomposed to hydrogen cyanide and a transitory cyanate of V

(V)

This compound then can proceed by one of three pathways: (1) it can react with water to form a carbamate; (2) it can react with another alcohol to form a dialiphatic, dialicyclic, diaryl., aliphatic aryl, etc. imidocarbonate; or (3) it can rearrange upon heating to form an ester of isocyanic acid. Although the reaction can be divided into these several steps, in effect the reaction proceeds in one vessel from cyanogen to carbamate and/or imidocarbonate. Pathways 1 and 2 generally dominate over pathway 3. The imidocarbonate of pathway 2 can further react with water to form ammonia and a carbonate

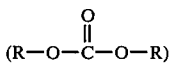

but this reaction is typically made after the imidocarbonate is separated from the reaction product.

The following are illustrative examples of certain specific embodiments of this invention. Unless otherwise noted, all parts and percentages are by weight.

SPECIFIC EMBODIMENTS

Example 1

In a 1 liter stainless steel Parr autoclave was placed 50 ml of 95% ethanol (0.815 moles ethanol and 0.11 moles water), 250 ml acetonitrile and 1.2 ml concentrated hydrochloric acid (containing 0.014 moles HCl and 0.05 moles water). The system was flushed with nitrogen and then 0.12 moles of cyanogen gas was metered into the system at 25° C. After stirring at room temperature for 24 hrs, the reaction mixture was purged with nitrogen to remove toxic gases and the autoclave opened. After vacuum stripping (45° C., 0.5 mm) the liquid product was found to contain substantial quantities of ethyl carbamate

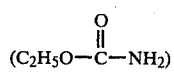

and diethyl imidocarbonate

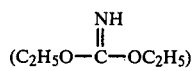

as identified by the infrared spectra of trapped gas chromatographic peaks. A sample of the product heated in an infrared cell at 165° C. to 187° C. showed the formation of an isocyanate ($V_{NCO}=2300$ cm$^{-1}$).

Example 2

In a 1 liter stainless steel autoclave was placed 50 ml of 95% ethanol, 250 ml acetonitrile and 1.0 gruthenium chloride. The system was flushed with nitrogen and then 0.18 moles of cyanogen gas was metered into the system. The reaction mixture was stirred for 8 hrs at 21° C. to 25° C. followed by heating to 92° C. over a period of 2.4 hrs. The product recovered after filtering and vacuum stripping was found to contain ethyl carbamate and diethyl imidocarbonate.

Example 3

In a 1 liter stainless steel autoclave was placed 300 ml anhydrous acetonitrile, 10 g (0.11 mole) neopentyl alcohol and 2 ml concentrated hydrochloric acid (containing 0.024 moles HCl and 0.083 moles water). The system was flushed with nitrogen and then 0.14 moles cyanogen gas was metered into the system. After stirring for 4 hrs at room temperature followed by heating to 108° C. over a period of 8.6 hrs, the product was recovered in the usual fashion and found to contain dineopentyl imidocarbonate

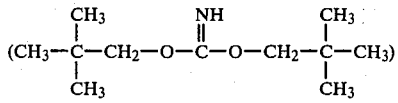

which was hydrolyzed to dineopentyl carbonate. A sample of the product heated in an infrared cell at 180° C. to 195° C. showed the formation of an isocyanate ($V_{NCO}=2300-2330$ cm$^{-1}$).

Example 4

In a 1 liter stainless steel autoclave was placed 250 ml acetonitrile, 50 ml (1.24 moles) methanol and 2 ml concentrated hydrochloride acid. The system was flushed with nitrogen and then 0.49 moles of cyanogen gas was metered into the system. After stirring for 5 hrs at room temperature followed by heating to 102° C. over a period of 12 hrs, the product was recovered in the usual fashion and found to contain crystals of methyl carbamate. The liquid product heated in an infrared cell at 137° C. showed the formation of methyl isocyanate ($V_{NCO}=2284$ cm$^{-1}$).

Example 5

In a 1 liter stainless steel autoclave was placed 250 ml acetonitrile, 50 ml (1.24 moles) methanol and 3.2 g. Norton Zeolon BPS-91 (an H$^+$-molecular sieve activated at 260° C. to 300° C. overnight). The system was flushed with nitrogen and then 0.62 moles of cyanogen gas was metered into the system. After stirring for 4 hrs at room temperature followed by heating to 98° C. over a period of 8 hrs, the product was recovered in the usual fashion and found to contain methyl carbamate and dimethyl imidocarbonate by gas chromatographic analysis.

Example 6

In a 1 liter stainless steel autoclave was placed 300 ml acetonitrile, 12.5 ml (0.31 mole) methanol and 5.0 g boron phosphate (P/B=1.5). The system was flushed with nitrogen and then 0.37 moles of cyanogen gas was metered into the system. After stirring for 4 hrs at room temperature followed by heating to 95° C. over a period of 8 hrs, the product was recovered in the usual fashion and found to contain methyl carbamate and dimethyl imidocarbonate by gas chromatographic analysis.

Example 7

In a 1 liter stainless steel autoclave was placed 300 ml acetonitrile, 2 ml concentrated hydrochloric acid and 10 g (0.11 moles) phenol. The system was flushed with nitrogen and then 0.25 moles of cyanogen gas was metered into the system. After stirring for 4 hrs at room temperature followed by heating to 107° C. over a period of 8 hrs, the product was recovered in the usual fashion and found to contain diphenyl imidocarbonate. A sample of product heated in an infrared cell at 136° C. showed the formation of an isocyanate ($V_{NCO}=2325$ cm$^{-1}$).

Example 8

In a 1 liter stainless steel autoclave was placed 300 ml acetonitrile, 10 g (0.094 moles) diethylene glycol and 2 concentrated hydrochloric acid. The system was flushed with nitrogen and then 0.25 moles cyanogen gas was metered into the system. After stirring at room temperature for 4 hrs, followed by heating to 105° C. over a period of 8 hrs, the product was recovered in the usual fashion and found to contain an imidocarbonate. Heating a sample of the product in an infrared cell at 107° C. to 190° C. gave an isocyanate ($V_{NCO}=2320$ cm$^{-1}$).

Although this invention has been described in considerable detail by the preceeding examples, the purpose of this detail is for illustration only and it is understood that various changes and modifications can be had without departing from the spirit and scope of the appended claims.

What is claimed is:

1. A process for the manufacture of a carbamate of the formula

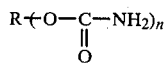  (I)

the process comprising contacting an alcohol of the formula

  (II)

with cyanogen and water in the presence of a dipolar, aprotic solvent and an acid catalyst, where R is an aliphatic, alicyclic or aryl radical and n is a positive integer.

2. A process for the manufacture of an imidocarbonate of the formula

  (III)

the process comprising contacting an alcohol of the formula

  (IV)

with cyanogen in the presence of a dipolar, aprotic solvent and an acid catalyst, where R is an aliphatic, alicyclic or aryl radical.

3. The process of claim 1 where R is an aliphatic or alicyclic radical of 1 to 30 carbon atoms or a phenyl radical and n is 1-6.

4. The process of claim 2 or 3 where the alcohol is a saturated, primary aliphatic alcohol.

5. The process of claim 2 or 3 where the solvent is selected from the group consisting of aliphatic, alicyclic and aromatic nitriles, ethers, sulfones and phosphoamides.

6. The process of claim 5 where the solvent is selected from the group consisting of acetonitrile, propionitrile, butyronitrile, adiponitrile, benzonitrile, tolunitrile, tetrahydrofuran, dioxane, dimethoxymethane, glyme, diglyme, anisole, tetramethylene sulfone, dipropyl sulfone and hexamethyphosphoamide.

7. The process of claim 6 where the catalyst is selected from the group consisting of boron trifluoride, sulfur dioxide, sulfur trioxide, hydrogen fluoride, sulfuric acid, phosphoric acid, hydrogen bromide, hydrogen chloride, hydrogen iodide, aluminum phosphate, zinconium phosphate, calcium nickel phosphate, phosphotungsidic acid, phosphomolybdic acid, phosphothallilic acid and acid forms of zeolites and in exchange resins.

8. The process of claim 7 where the contacting is conducted at a temperature of about 15° C. to about 250° C.

9. The process of claim 8 where the alcohol is present in an excess of the stoichiometric requirement based on the cyanogen.

10. The process of claim 1 where n is one.

11. A process for the manufacture of a carbonate of the formula

  (V)

the process comprising
(A) contacting an alcohol of the formula

  (IV)

with cyanogen in the presence of a dipolar, aprotic solvent and an acid catalyst to form an imidocarbonate of the formula

  (III)

and
(B) contacting the imidocarbonate of (A) with water, where R is an aliphatic, alicyclic or aryl radical.

* * * * *